(12) United States Patent
Kellar et al.

(10) Patent No.: US 6,198,861 B1
(45) Date of Patent: Mar. 6, 2001

(54) METHOD OF USING THIN-CLAD NEAR INFRARED TRANSPARENT OPTICAL GLASS FIBERS AS EVANESCENT WAVE SENSORS

(75) Inventors: Jon J. Kellar; William M. Cross; Farrah J. Johnson; Michael E. Connell, all of Rapid City, SD (US)

(73) Assignee: South Dakota School of Mines and Technology, Rapid City, SD (US)

( * ) Notice: Subject to any disclaimer, the term of this patent is extended or adjusted under 35 U.S.C. 154(b) by 0 days.

(21) Appl. No.: 09/226,217

(22) Filed: Jan. 7, 1999

(51) Int. Cl.[7] ........................................... G01B 9/02
(52) U.S. Cl. ........................ 385/30; 385/31; 356/35.5
(58) Field of Search ............................. 356/35.5; 385/30, 385/31

(56) References Cited

U.S. PATENT DOCUMENTS

| | | |
|---|---|---|
| Re. 33,789 | 1/1992 | Stevenson . |
| 3,253,896 | 5/1966 | Woodcock et al. . |
| 3,460,893 | 8/1969 | Wilks, Jr. . |
| 3,942,965 | 3/1976 | Osagawa et al. . |
| 5,494,798 | 2/1996 | Gerdt et al. . |
| 5,525,800 | 6/1996 | Sanghera et al. . |
| 5,585,634 | 12/1996 | Stevenson et al. . |
| 5,712,934 | 1/1998 | Johnson . |

*Primary Examiner*—Robert H. Kim
(74) *Attorney, Agent, or Firm*—Nixon & Vanderhye PC; Frank P. Presta

(57) ABSTRACT

A method of analyzing a chemical reaction in a material including the steps of embedding in a material an optical fiber having a cladding along substantially the entire length thereof that is in contact with the material, transmitting light through the optical fiber, and performing evanescent wave spectroscopy on the light transmitted through the optical fiber. The optical fiber preferably has a core 10–30 $\mu$m in diameter and a cladding that is on the order of 1 $\mu$m thick.

15 Claims, 6 Drawing Sheets

METHOD OF USING THIN-CLAD NEAR INFRARED TRANSPARENT OPTICAL GLASS FIBERS AS EVANESCENT WAVE SENSORS

The present invention is directed to optical fiber evanescent wave sensors and, more particularly, to a novel use of a cladded optical fiber incorporated into a composite material and used as an evanescent wave sensor.

BACKGROUND OF THE INVENTION

Fiberglass/polymer-matrix composites have seen increased industrial use due to their low density, versatility, and specific strength values. However, these composites consist of two highly dissimilar materials, which, at an interface between the fiber and matrix, form an interphase region. This interphase region typically is the weakest point in the composite due to insufficient bonding. To alleviate this problem, industrially, silane coupling agents have been applied via surface treatments to the fiber reinforcements. These agents have been shown to increase the strength and hygrothermal stability of the composites. In view of the increasing reliance on such polymer matrix composites, a need exists for an improved understanding of the chemical inter-reactions occurring within the interphase region, which now further comprises the silane coupling agents.

One technology that is particularly useful in monitoring and analyzing a fluid is spectrometric examination of light that passes through optical fibers disposed in the fluid, wherein the fibers act as evanescent wave sensors. An evanescent wave is electromagnetic radiation that results from the propagation of light through a light-conducting medium and that is present outside of the light-conducting medium. When light is transmitted through a high index of refraction medium (an optical fiber) the evanescent wave (or field) is produced in an adjacent lower index of refraction material and has intensity only within a fractional wavelength distance from the interface between the two mediums. Thus, spectrometric examination of light passed through optical fibers disposed in the fluid can reveal characteristics and properties associated with that fluid, at least immediately adjacent the optical fiber.

U.S. Pat. No. 5,712,934 to Johnson, for example, discloses an optical sensor using an optical fiber. However, the sensor operates on a principal requiring a return bend in the fiber, which leads to relatively complicated structures. Also, cladding that surrounds the optical fiber must be removed in the sensing regions to promote proper interaction between the optical fiber and the fluid being analyzed. Additionally, the fiber used by Johnson is not transparent in the infrared wavelength region and, accordingly, cannot be used with infrared spectroscopy, which is desirable in studying polymers, for example.

Similarly, U.S. Pat. No. 5,525,800 to Sanghera et al. and U.S. Pat. No. 5,585,634 to Stevenson et al. disclose optical fibers used as sensors wherein the cladding surrounding the fiber core must be removed in the sensing area. Further, according to Sanghera et al., a polymer is disposed in the region where the fiber has been stripped of its cladding, the polymer having a lower refractive index than that of the core of the fiber, and having an affinity for chemicals that may be of interest.

The present inventors have also previously researched the use of optical fibers as evanescent wave sensors. Particularly, optical fibers incorporated in polymer matrix composites have been studied. Studies were conducted with Polymicro Technology FIP 100/120/140 fibers consisting of a 100 $\mu$m diameter fused silica core, a 10 $\mu$m fluorine-doped fused silica cladding and a 10 $\mu$m polyimide buffer. As in the prior art patents discussed above, the buffer and cladding were removed from a portion of the fibers to allow the fused silica core to be used as a model reinforcement as well as an evanescent wave sensor.

The exposed silica core was transparent over the 12,000 $cm^{-1}$ to 4,000 $cm^{-1}$ near infrared region. In the study using this sensor system the bulk curing of Epo-Tek 328 (available from Epoxy Technology, Inc., Billerica, Mass., and a diamine hardener was investigated in situ using a Fourier Transform Infrared (FT-IR) spectrometer. In a subsequent investigation, $\gamma$-aminopropyltrimethoxy silane ($\gamma$-APS, available from Sigma Chemical Co., St. Louis, Mo., coupling agent was adsorbed from aqueous solution onto the fibers, which were then immersed in Epo-Tech 328 in the absence of a curing agent. Heat was added to this system to promote reaction of the epoxy with the amino silane.

A band was present at 4925 $cm^{-1}$ due to the stretching-bending combination of the —$NH_2$ of the $\gamma$-APS. This band was seen to decrease with time at elevated temperature when immersed in the epoxy. Such a decrease was expected as hydrogen atoms are abstracted from the —$NH_2$ by reaction with the epoxy ring of the resin. A greater fraction of the —$NH_2$ groups reacted when lower initial $\gamma$-APS solution concentrations were used to adsorb the $\gamma$-APS.

These findings are significant in that this system allows for direct monitoring of interaction between an epoxy resin and an aminosilane coupling agent adsorbed to silica fibers. However, this system does not adequately simulate a typical industrial composite for a number of reasons. First, the diameter of commonly used glass fibers is around 10 $\mu$m, whereas the silica core of the FIP fibers is 100 $\mu$m, an order of magnitude greater than the industrial fibers. Second, fiber size and flexibility are of concern because of possible industrial sensing applications. Relatively large fibers act to weaken the composite, as they are very brittle upon removal of the buffer and cladding.

Third, the composition of a typical industrial fiber (fiberglass) is approximately 55% $SiO_2$, 16% CaO, 15% $Al_2O_3$, 10% $B_2O_3$, and 4% MgO, whereas the fused silica fibers are greater than 98% $SiO_2$. The composition of the fiber is relevant because it has been shown previously that substrate effects can significantly influence composite properties. In this regard, see F. Garbassi, E. Occhielo, C. Bastioli and G. Romano, Journal of Colloid and Interface Science, 117, No. 1 (1987); D. J. Dawson and F. R. Jones, "The Role of Silane Treatment on the Retained Interlaminar Shear Strengths Aqueous Conditioned Glass Fiber Composites," in *Controlled Interphases in Composite Materials*, H. Ishida, Ed. (Elsevier Science Publishing Co., 1990), pp. 409–415; and T. H. Elmer, "Glass Surfaces," in *Silyated Surfaces*, D. E. Leyden and W. T. Collins, Eds. (Gordon and Breach Publishers, 1980), pp. 1–30. Significantly, it was shown that quartz exhibited much different bonding characteristics when exposed to a silane coupling agent than did glass and alumina and that alkali ions influence interphase properties. See, for example, Garbassi et al. and Dawson et al., cited above.

Optically, evanescent wave sensing requires the refractive index of the interphase adjacent the fiber to be less than the refractive index of the fiber. The previously studied FIP fibers have a refractive index of 1.4 (near-IR), whereas most epoxies have a refractive of at least 1.45. To alleviate this problem, model low refractive index epoxies such as fluorinated polymer must be used in combination with the FIP fiber system, thereby adding cost and limiting the ability of that system from analyzing different types of epoxies.

SUMMARY OF THE INVENTION

It is therefore an object of the present invention to overcome the drawbacks of the prior art methods discussed above and provide a method of analyzing composite materials with a cladded optical fiber that operates as an in situ evanescent wave sensor.

It is a further object, but not a necessary requirement, of the present invention to provide a method wherein the optical fiber used has a size comparable with fibers used in the composite material.

Still another object of the present invention is to provide a method of analyzing material with infrared spectrometry via an optical fiber having substantially no micro-bends in the length thereof that is in contact with the material that is being studied.

These and other objects of the invention are achieved by providing a method of analyzing a chemical reaction in a material, comprising the steps of embedding in a material an optical fiber having a cladding along substantially the entire length thereof that is in contact with the material, transmitting light through the optical fiber, and performing evanescent wave spectroscopy on the light transmitted through the optical fiber.

Preferably, the overall diameter of the optical fiber is about 25 $\mu$m, a core of the optical fiber is about 10–30 $\mu$m and the cladding is about 1 $\mu$m, although any fiber system having a cladding thin enough to allow sufficient energy in the evanescent wave outside the cladding will behave in a similar manner.

Also in accordance with present invention, the optical fiber is disposed substantially straight through the material, thereby avoiding intricate bending or bent structures.

Preferably the core of the optical fiber comprises flint glass and the cladding of the optical fiber comprises soda-lime.

In accordance with the method of the present invention, the optical fiber is incorporated in a polymer matrix composite, which composite includes fiberglass.

Further in accordance with the method of the present invention, in situ monitoring of polymer curing is made possible by combining a clad optical fiber with the polymer, transmitting light through the optical fiber, curing the polymer, and monitoring the light transmitted through the optical fiber.

The method preferably further comprises continuously monitoring any infrared evanescent wave spectra throughout the curing step.

BRIEF DESCRIPTION OF THE DRAWINGS

The present invention will be more fully understood upon reading the following Detailed Description of the Preferred Embodiments in conjunction with the accompanying figures, in which reference numerals are used consistently to indicate like elements, and in which.

DETAILED DESCRIPTION OF THE PREFERRED EMBODIMENTS

Figure 1:
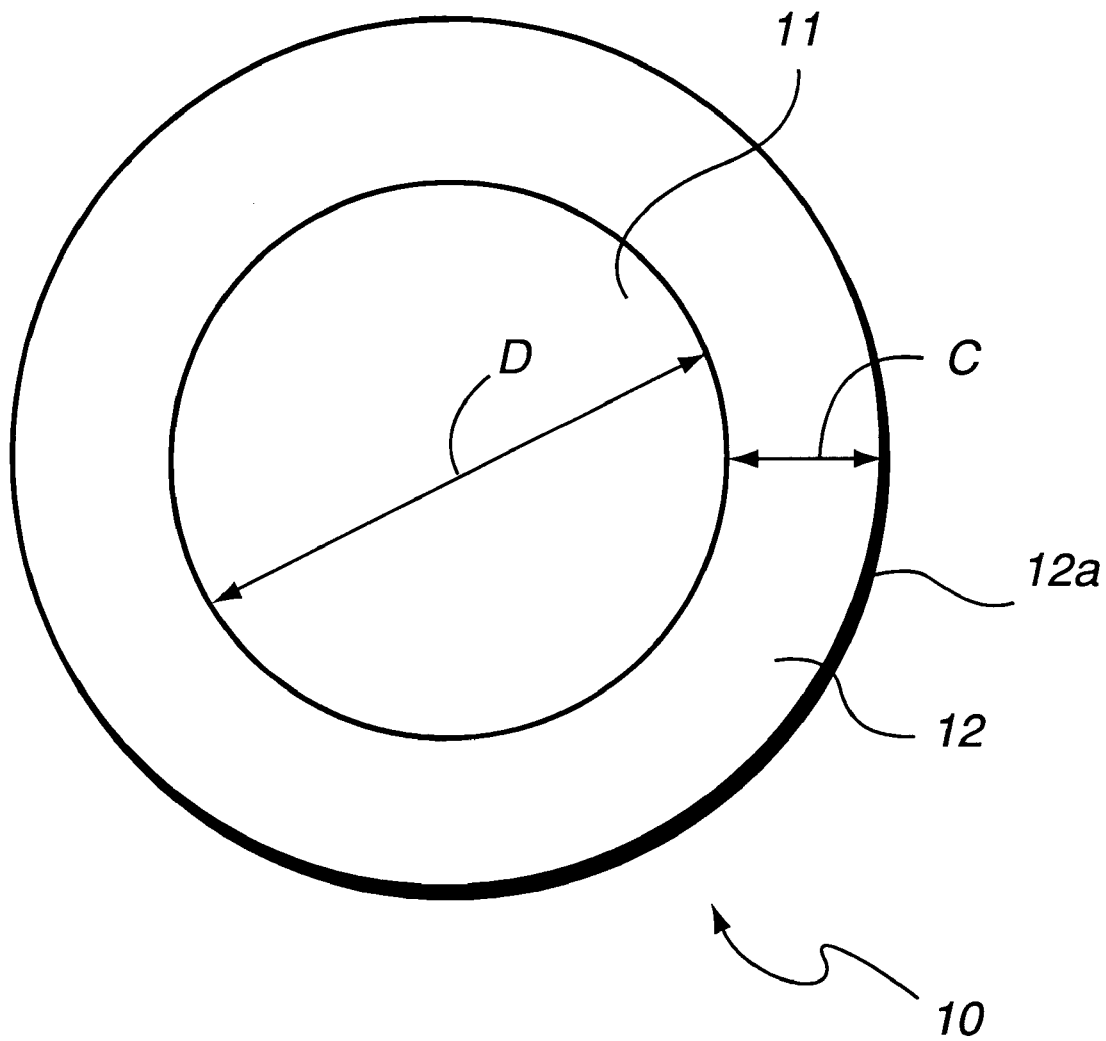
FIG. 1 illustrates an optical fiber that is operable with the method of the present invention.

The present invention will now be described with reference to the figures. In accordance with the present invention, a fiber sensor which more closely resembles actual industrial glass fibers is implemented as an evanescent wave sensor. As shown in FIG. 1, the fiber 10 preferably has a 23 $\mu$m diameter D flint-glass core 11 with a 1 $\mu$m (dimension C) soda-lime cladding 12. The soda-lime cladding 12 has an index of refraction of 0.55.

The combined dimensions of the 23 $\mu$m core 11 and 1 $\mu$m cladding 12 results in an overall 25 $\mu$m diameter fiber which is closer to industrial fibers than the above-discussed FIP fibers, which typically have a diameter on the order of 140 $\mu$m. The composition of the core 11 preferably is 54% $SiO_2$, 1% $Na_2O$, 37% PbO, and 8%$K_2O$. The cladding 12 preferably comprises 74% $SiO_2$, 16% $Na_2O$, 5% CaO, 1% $Al_2O_3$, and 4%MgO. It is noted that the cladding 12 of the fiber 10 is closer in composition to industrial E-glass fibers than the diffused silica core of the FIP fibers, making the cladding 12 a more relevant substrate for examination of polymer chemistry phenomenon associated with a particular fiberglass composite system being investigated. An optical fiber 10 that is particularly compatible with the method the present invention may be obtained from Dolan-Jenner Inc., Lawrence, Mass.

The refractive index of optical flint glass (core 11) is approximately 1.61, and that of soda-lime glass (cladding 12) is approximately 1.51, both higher than the refractive index of the FIP fiber core. The optical fiber 10 is also relatively more flexible than the fused silica FIP fibers, greatly increasing the ease of handling.

Because the cladding 12 on the flint glass core of the fiber 10 is only on the order of 1 $\mu$m thick, any evanescent wave should theoretically extend beyond the cladding, allowing sampling of the interphase adjacent the surface of the cladding 12. The strength of the evanescent wave at the cladding surface 12a can be calculated from the decay of the evanescent wave. For optical fibers, the energy of the evanescent wave decays as a Bessel function. This Bessel function can be approximated by an exponential decay such that $$E(z)=E(0)\exp(-z/d_p)$$

where E is the amplitude of the electric field, z is the distance from the surface, and dp is the penetration which is dependent on the mode, and hence the angle of light propagation. For the fiber 10 used in accordance with the present invention, about 20% of the original electric field is present at the cladding/air interface, although the precise amount depends upon the mode.

Initially, to determine if an evanescent wave is strong enough to sample material adjacent the soda-lime cladding 12, a bundle of approximately 25 fibers 10 was placed in water and a Biorad Digilab FTS 40A spectrometer was used to monitor for the presence of a broad water band at approximately 5,200 $cm^{-1}$. It should be noted that the transmission range of the fiber bundle is approximately 12,000 $cm^{-1}$ to 4,500 $cm^{-1}$. The 5,200 $cm^{-1}$ band was indeed present, indicating either the propagation of the evanescent wave into the water or the penetration of water into the fiber cladding. To disprove the latter possibility, the fibers 10 were dried using hot air and another spectrum obtained. The water band disappeared, indicating water had not penetrated below the surface of the cladding 12. In view of the foregoing, and in accordance with the present invention, it was concluded that a fiber 10 could be used as an evanescent wave sensor without removing the cladding, a highly beneficial feature not possible with the FIP fibers.

The presence of water on the surface of the fibers could also be due to an incoherent cladding, allowing the evanescent wave to propagate from the core 11 to water in some areas. The fibers 10 were examined using a Scanning Electron Microscope (SEM) for consistency and homogeneity in the cladding 12 coverage. A chemical analysis of the fiber surface 12a along both the length and cross-section were performed to verify that no areas of the core 11 were exposed along the fiber 10. Both the visual and chemical examination indicated no exposed core areas. In fact, the visual examination showed the cladding 12 to be coherent. In accordance with the present invention, it is believed that the homogeneity of the cladding 12 proves that water was not present at the core surface, which indicates the water present in the spectrum obtained from this fiber system was due to the evanescent wave passing through the cladding 12 into the water. This evidence further verifies the ability of these fibers 10 to be used as evanescent wave sensors without cladding removal, a significant advance over prior art evanescent wave sensors.

Figure 2:
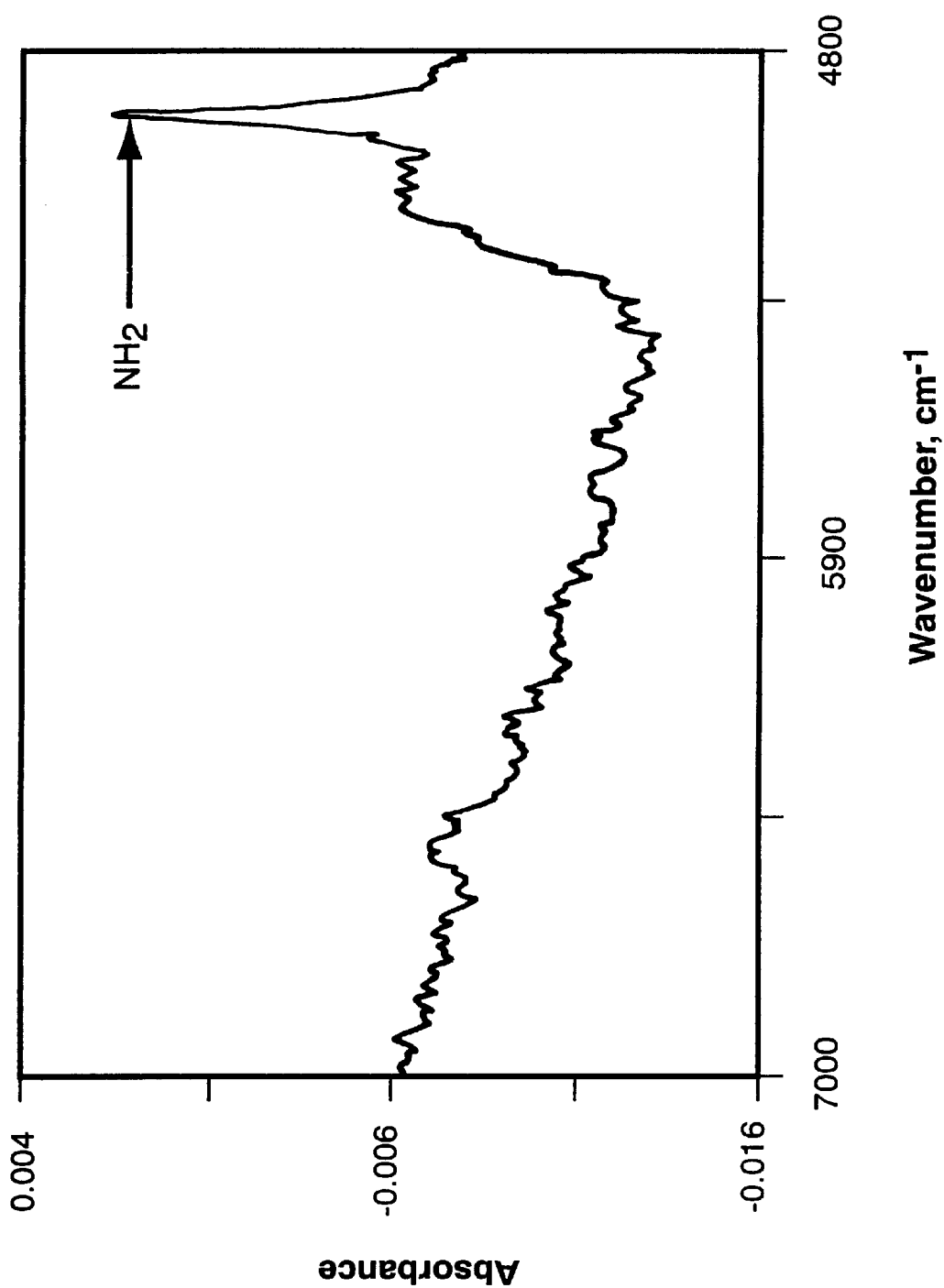
FIGS. 2 and 3 show experimental results of infrared spectrometry using an evanescent sensor in accordance with the method of the present invention.

The ability of the fibers 10 to serve as sensors for composite materials was demonstrated by placing the fibers in a 5% γ-APS solution to examine for the presence of adsorbed silane. FIG. 2 shows the spectrum obtained when the fibers were immersed in the silane solution and then dried. The —$NH_2$ band at 4925 $cm^{-1}$ as described earlier, was present, as well as other expected γ-APS bands.

Figure 3:
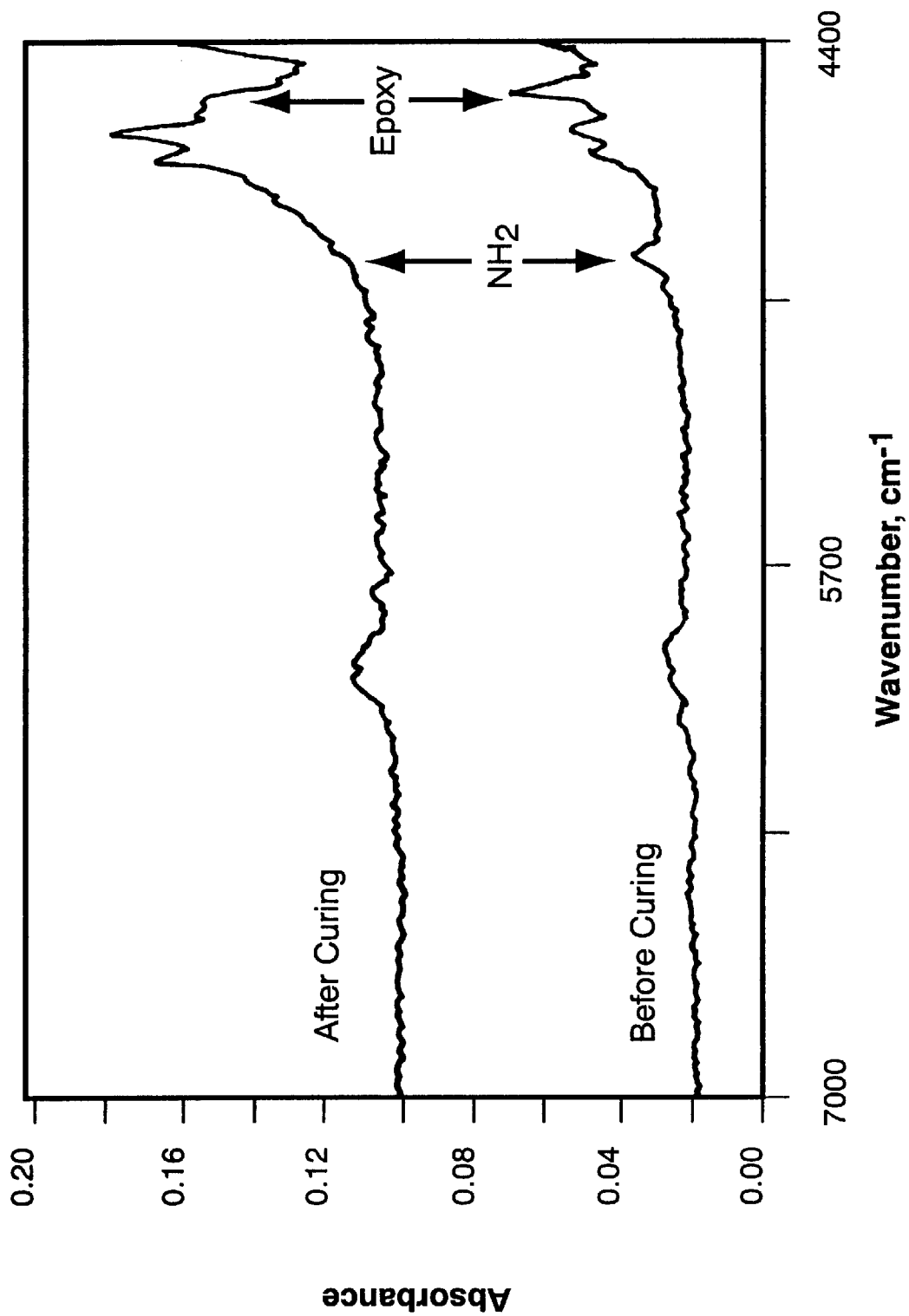

As explained earlier herein, the FIP fiber sensors used in previous studies required the use of a fluorinated, lower refractive index epoxy to monitor polymer curing, due to the relatively low refractive index of the FIP core. Such polymers are not widely used industrially, and as such, greatly limit the use of FIP-based sensor systems. However, given the higher refractive indexes of the fibers 10 used in the method of the present invention, cure monitoring of non-fluorinated industrial polymers becomes possible. In this regard, a soda-lime clad optical fiber bundle was immersed in Shell EPON 828 epoxy with the manufacturer recommended volume of Shell EPICURE 3282 aliphatic amine hardener. FIG. 3 depicts the in situ spectra that resulted as a function of time at 70° C. These spectra illustrate the decrease with time of the bands at 4925 $cm^{-1}$ and 4525 $cm^{-1}$. These bands are combination bands due to —$NH_2$ and —$CH_2$ (adjacent the epoxy moiety), and are both expected to decrease according to generally-understood epoxy curing reactions. Accordingly, the use of the fibers 10 in accordance with the method of the present invention appears to be ideal for monitoring polymer curing.

In accordance with the preferred embodiment of the method of the present invention, the total fiber diameter is preferably relatively close to that of reinforcing glass fibers (fiberglass). If the fibers are much larger than typical reinforcing fibers, stress concentration and premature failure of the material may result. Therefore, the preferred fiber diameter is between 30–10 μm. The cladding material preferably is thin enough, as explained above, to be coherent over the core yet thin enough to allow penetration of the evanescent wave through the cladding 12. Preferable cladding thickness is approximately 1 μm, since thicker cladding may not allow "leaking" of the evanescent wave and, as a result, sensitivity would be diminished.

Figure 4:
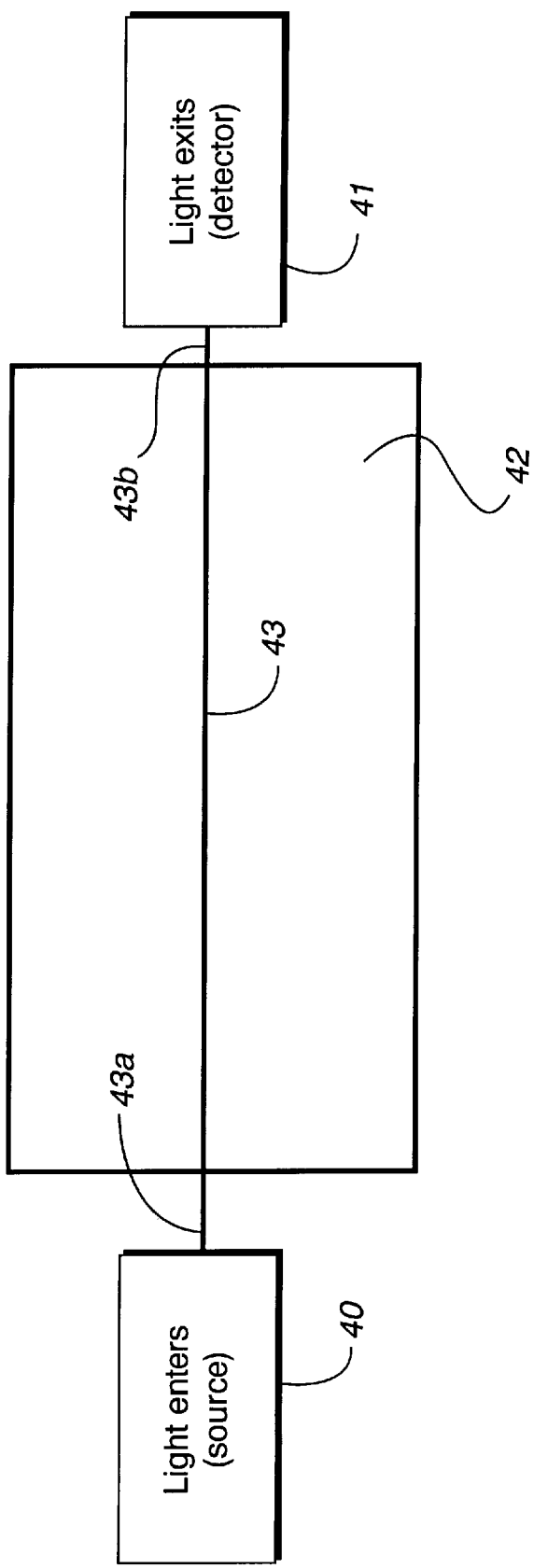
FIG. 4 illustrates the use of the optical fiber in a matrix material in accordance with the method of the present invention.

FIG. 4 shows how the optical fibers 10 are used in accordance with the present invention. An optical fiber bundle 43 is incorporated into a matrix material 42. A light source 40 injects light into the fiber bundle 43 and a light detector 41, an infrared spectrometer, for example, is arranged at the other end of the fiber bundle 43. As is easily seen in FIG. 4, no bending of the fiber is necessary to use the fibers as evanescent wave sensors. Moreover, as has been explained throughout, the cladding material 12 need not be removed to successfully use the fibers 10 as evanescent wave sensors. Thus, in accordance with the present invention, fibers 10 can easily be incorporated into a polymer matrix composite material to monitor and analyze the interphase region between the fiber and polymer matrix. That is, in situ analysis of composite materials can be accomplished without appreciable degradation to the ultimately manufactured part, since the overall diameter of the optical fibers used as evanescent wave sensors closely match the diameter of fibers, e.g. fiberglass, typically used for the bulk material. It should be noted that a single or a plurality of evanescent wave sensors (fibers) can be incorporated into the composite material. No particular density of fibers is necessary to perform spectrometry. When analysis is completed, ends 43a, 43b of the optical fiber 43 are preferably removed, thereby providing smooth edges to any completed part, should that be desired.

Figure 5A:
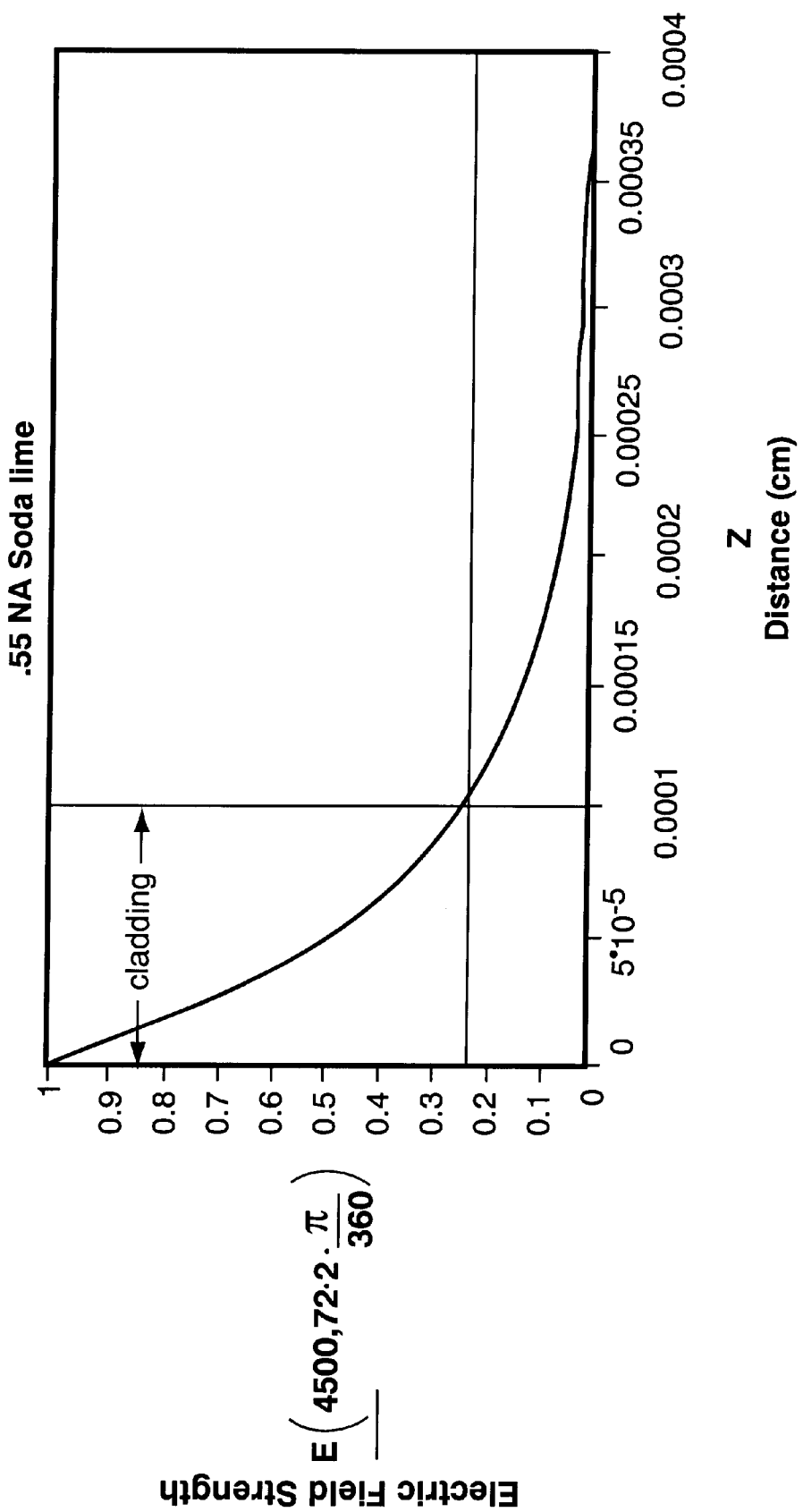
FIGS. 5A and 5B show normalized electric field strength as a function of distance from fiber core for soda-lime clad fibers and borosilicate clad fibers, respectively.
Figure 5B:
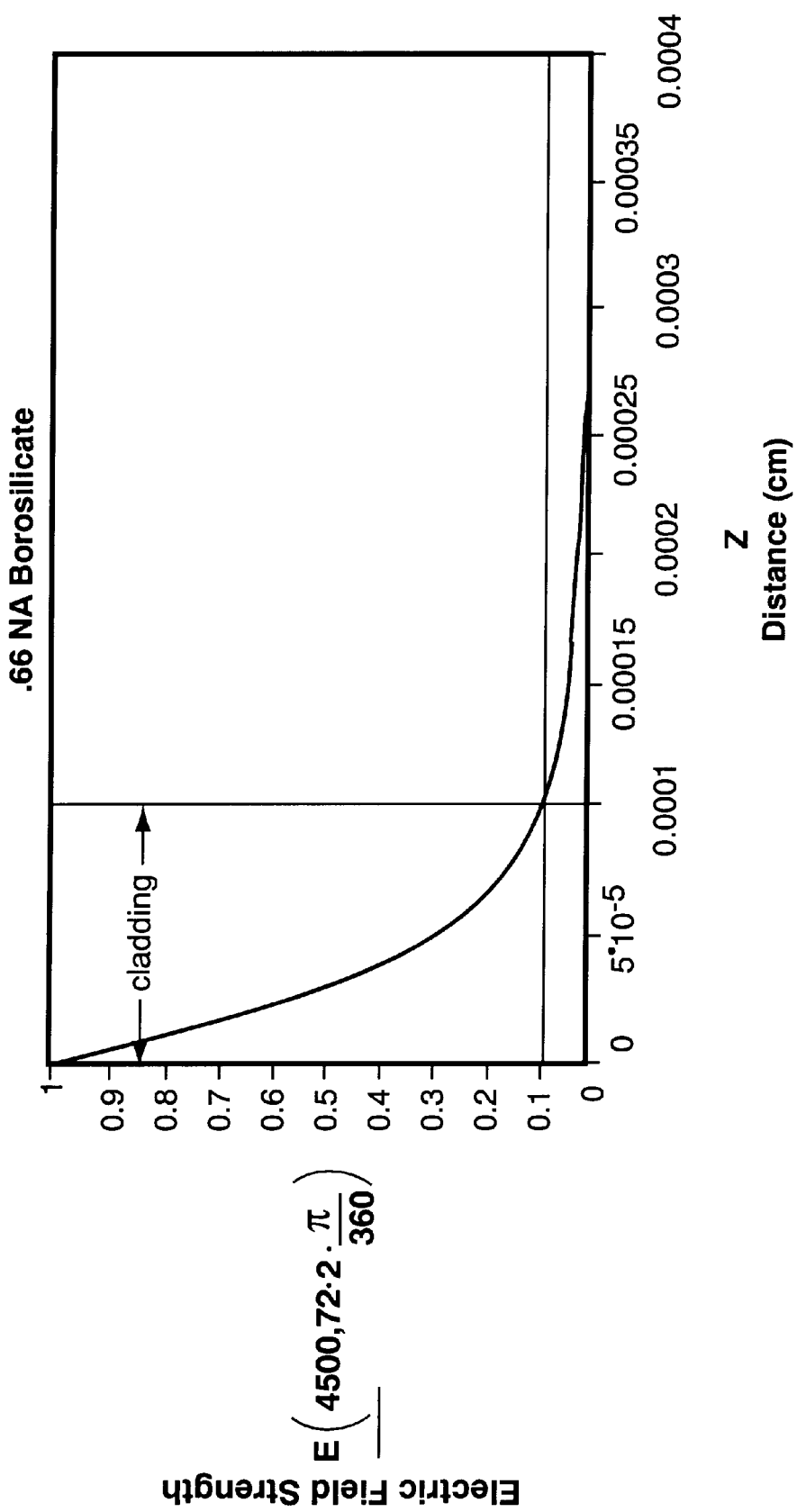

FIGS. 5A and 5B show normalized electric field strengths as a function of distance from a fiber core with a soda-lime clad fiber (FIG. 5A) and a borosilicate clad fiber (FIG. 5B). If the refractive index, n, of the cladding 12 is too large, the evanescent wave will not propagate through the cladding 12 even when it is relatively thin. For example, if the cladding material is borosilicate, n=1.47, and not soda-lime, n=1.51, evanescent wave sensing is too weak to give adequate infrared wave spectra. Thus, as shown in FIG. 5A, the evanescent wave extends beyond the soda-lime cladding with approximately 23% of electric field strength remaining at a distance of 1 μm from the core/cladding interface (the thickness of the cladding), allowing sampling of the interphase adjacent the surface of the cladding. In contrast, with a borosilicate clad fiber, it can be seen that the electric field strength at 1 μm is less than 10%, indicating that sensing beyond the cladding is extremely difficult.

The preferred fiber type operable with the method of the present invention is a metal oxide glass due to substrate considerations. Other fiber types have much different adhesion properties so that, if embedded in a polymer, drastically different reinforcing properties may result compared to embedded fiberglass fibers. The fiber 10 described herein has substrate chemistry very similar to the fiberglass fibers so any dissimilar material concern is greatly diminished. On the other hand, if fiber adhesion is not a concern, alternate fiber core/cladding materials that can be used include fused silica materials, chalcoganide glass, halides and the like. Furthermore, various combinations of these materials can be used as long as the optical constraints delineated herein are met.

In summary, as industrial employment of fiberglass/polymer/matrix composites has increased significantly due to their physical and chemical properties, improvements upon these composites necessitate a more complete understanding of the chemical interactions at the fiber-matrix interphase. The present invention provides a method of analysis of the interphase region via evanescent wave spectroscopy by incorporating cladded optical fibers into the substrate itself. Use of flint-glass fibers with an intact soda-lime cladding simulates closely industrial fiberglass while simultaneously serving as a convenient sensor without the necessity of cladding removal. As a result, the method in accordance with the present invention may be utilized as a relevant mode for analysis of polymer chemistry of polymer matrix composites.

The present invention has been described in terms of presently preferred embodiments so that an understanding of the present invention can be conveyed. The present invention should therefore not be seen as limited to the particular embodiments described herein. Rather, all modification, variations, or equivalent arrangements that are within the scope of the attached claims should be considered to be within the scope of the invention.

What is claimed is:

1. A method of analyzing a chemical reaction in a material, comprising the steps of:

embedding in a material an optical fiber having a cladding along substantially the entire length thereof that is in contact with the material, said cladding being of a thickness to allow an evanescent wave to extend beyond the cladding to sample the material adjacent the fiber;

transmitting light through the optical fiber; and performing evanescent wave spectroscopy on the light transmitted through the optical fiber.

2. The method of claim 1, wherein a core of the optical fiber is about 10–30 $\mu$m and the cladding is about 1 $\mu$m.

3. The method of claim 1, wherein the optical fiber is disposed substantially straight through the material.

4. The method of claim 1, wherein a core of the optical fiber comprises flint glass.

5. The method of claim 1, wherein the cladding of the optical fiber comprises soda-lime.

6. The method of claim 1, wherein the material is a polymer matrix composite.

7. The method of claim 6, further comprising analyzing the polymer region adjacent the optical fiber.

8. A method of in situ monitoring of polymer chemistry, comprising the steps of:

combining an optical fiber having a cladding along substantially the entire length thereof with the polymer, the cladding being of a thickness to allow an evanescent wave to extend through it;

transmitting light through the optical fiber;

curing the polymer; and monitoring the light transmitted through the optical fiber.

9. The method of claim 8, further comprising monitoring evanescent wave spectra of the Light transmitted through the optical fiber.

10. The method of claim 8, further comprising continuously monitoring the evanescent wave spectra throughout the changes in polymer chemistry.

11. The method of claim 8, further comprising conducting infrared spectroscopy.

12. The method of claim 8, further comprising maintaining the optical fiber in a substantially straight line in the polymer.

13. The method of claim 8, wherein the optical fiber has an overall diameter of about 10–30 $\mu$m.

14. The method of claim 8, wherein the optical fiber comprises a flint glass core and a soda-lime cladding.

15. The method of claim 13 wherein the cladding is about 1 $\mu$m in thickness.

* * * * *